(12) United States Patent
Pollack et al.

(10) Patent No.: US 9,091,649 B2
(45) Date of Patent: Jul. 28, 2015

(54) INTEGRATED DROPLET ACTUATOR FOR GEL; ELECTROPHORESIS AND MOLECULAR ANALYSIS

(75) Inventors: Michael G. Pollack, Durham, NC (US); Vijay Srinivasan, Durham, NC (US); Zhishan Hua, Durham, NC (US); Hon Lung Chu, Durham, NC (US); Michael Hauser, Durham, NC (US); Allen Eckhardt, Durham, NC (US)

(73) Assignees: ADVANCED LIQUID LOGIC, INC., San Diego, CA (US); DUKE UNIVERSITY, Durham, NC (US)

( * ) Notice: Subject to any disclaimer, the term of this patent is extended or adjusted under 35 U.S.C. 154(b) by 686 days.

(21) Appl. No.: 13/508,300

(22) PCT Filed: Nov. 8, 2010

(86) PCT No.: PCT/US2010/055843
§ 371 (c)(1),
(2), (4) Date: Oct. 11, 2012

(87) PCT Pub. No.: WO2011/057197
PCT Pub. Date: May 12, 2011

(65) Prior Publication Data
US 2013/0059366 A1    Mar. 7, 2013

Related U.S. Application Data
(60) Provisional application No. 61/258,827, filed on Nov. 6, 2009.

(51) Int. Cl.
*G01N 27/447* (2006.01)
*B01L 7/00* (2006.01)
*B01L 3/00* (2006.01)

(52) U.S. Cl.
CPC .... *G01N 27/44791* (2013.01); *B01L 3/502792* (2013.01); *B01L 7/525* (2013.01);
(Continued)

(58) Field of Classification Search
CPC ................................. B01L 3/502784–3/502792
See application file for complete search history.

(56) References Cited

U.S. PATENT DOCUMENTS

| 4,636,785 A | 1/1987 | Le Pesant |
| 5,181,016 A | 1/1993 | Lee et al. |

(Continued)

FOREIGN PATENT DOCUMENTS

| JP | 2006329899 A | 12/2006 |
| JP | 2006329904 A | 12/2006 |

(Continued)

OTHER PUBLICATIONS

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

(Continued)

*Primary Examiner* — Alex Noguerola
(74) *Attorney, Agent, or Firm* — William A. Barrett; Ward & Smith, P.A.

(57) ABSTRACT

The invention is directed to a droplet actuator device and methods for integrating gel electrophoresis analysis with pre or post-analytical sample handling as well as other molecular analysis processes. Using digital microfluidics technology, the droplet actuator device and methods of the invention provide the ability to perform gel electrophoresis and liquid handling operations on a single integrated device. The integrated liquid handling operations may be used to prepare and deliver samples to the electrophoresis gel, capture and subsequently process products of the electrophoresis gel or perform additional assays on the same sample materials which are analyzed by gel electrophoresis. In one embodiment, one or more molecular assays, such as nucleic acid (e.g., DNA) quantification by real-time PCR, and one or more sample processing operations such as sample dilution is performed on a droplet actuator integrated with an electrophoresis gel. In one embodiment, an electrophoresis gel may be integrated on the top substrate of the droplet actuator.

47 Claims, 6 Drawing Sheets

(52) U.S. Cl.
CPC ...... *B01L3/502715* (2013.01); *B01L 2200/025* (2013.01); *B01L 2200/027* (2013.01); *B01L 2300/088* (2013.01); *B01L 2300/089* (2013.01); *B01L 2300/0887* (2013.01); *B01L 2300/161* (2013.01); *B01L 2400/043* (2013.01); *B01L 2400/046* (2013.01); *B01L 2400/0457* (2013.01)

(56) References Cited

U.S. PATENT DOCUMENTS

| | | | |
|---|---|---|---|
| 5,486,337 A | 1/1996 | Ohkawa et al. | |
| 6,063,339 A | 5/2000 | Tisone et al. | |
| 6,130,098 A | 10/2000 | Handique et al. | |
| 6,294,063 B1 | 9/2001 | Becker et al. | |
| 6,565,727 B1 | 5/2003 | Shenderov | |
| 6,773,566 B2 | 8/2004 | Shenderov | |
| 6,790,011 B1 | 9/2004 | Le Pesant et al. | |
| 6,911,132 B2 | 6/2005 | Pamula et al. | |
| 6,924,792 B1 | 8/2005 | Jessop | |
| 6,977,033 B2 | 12/2005 | Becker et al. | |
| 6,989,234 B2 | 1/2006 | Kolar et al. | |
| 7,052,244 B2 | 5/2006 | Fouillet et al. | |
| 7,068,367 B2 | 6/2006 | Stowbrawa et al. | |
| 7,163,612 B2 | 1/2007 | Sterling et al. | |
| 7,211,223 B2 | 5/2007 | Fouillet et al. | |
| 7,255,780 B2 | 8/2007 | Shenderov | |
| 7,328,979 B2 | 2/2008 | Decre et al. | |
| 7,329,545 B2 | 2/2008 | Pamula et al. | |
| 7,439,014 B2 | 10/2008 | Pamula et al. | |
| 7,458,661 B2 | 12/2008 | Kim et al. | |
| 7,531,072 B2 | 5/2009 | Roux et al. | |
| 7,547,380 B2 | 6/2009 | Velev | |
| 7,569,129 B2 | 8/2009 | Pamula et al. | |
| 7,641,779 B2 | 1/2010 | Becker et al. | |
| 7,727,466 B2 | 6/2010 | Meathrel et al. | |
| 7,727,723 B2 | 6/2010 | Pollack et al. | |
| 7,759,132 B2 | 7/2010 | Pollack et al. | |
| 7,763,471 B2 | 7/2010 | Pamula et al. | |
| 7,815,871 B2 | 10/2010 | Pamula et al. | |
| 7,816,121 B2 | 10/2010 | Pollack et al. | |
| 7,822,510 B2 | 10/2010 | Paik et al. | |
| 7,851,184 B2 | 12/2010 | Pollack et al. | |
| 7,875,160 B2 | 1/2011 | Jary | |
| 7,901,947 B2 | 3/2011 | Pollack et al. | |
| 7,919,330 B2 | 4/2011 | De Guzman et al. | |
| 7,922,886 B2 | 4/2011 | Fouillet et al. | |
| 7,939,021 B2 | 5/2011 | Smith et al. | |
| 7,943,030 B2 | 5/2011 | Shenderov | |
| 7,989,056 B2 | 8/2011 | Plissonier et al. | |
| 7,998,436 B2 | 8/2011 | Pollack | |
| 8,007,739 B2 | 8/2011 | Pollack et al. | |
| 8,041,463 B2 | 10/2011 | Pollack et al. | |
| 8,048,628 B2 | 11/2011 | Pollack et al. | |
| 8,075,754 B2 | 12/2011 | Sauter-Starace et al. | |
| 8,088,578 B2 | 1/2012 | Hua et al. | |
| 8,093,062 B2 | 1/2012 | Winger et al. | |
| 8,093,064 B2 | 1/2012 | Shah et al. | |
| 8,137,917 B2 | 3/2012 | Pollack et al. | |
| 8,147,668 B2 | 4/2012 | Pollack et al. | |
| 8,202,686 B2 | 6/2012 | Pamula et al. | |
| 8,208,146 B2 | 6/2012 | Srinivasan et al. | |
| 8,221,605 B2 | 7/2012 | Pollack et al. | |
| 8,236,156 B2 | 8/2012 | Sarrut et al. | |
| 8,268,246 B2 | 9/2012 | Srinivasan et al. | |
| 8,287,711 B2 | 10/2012 | Pollack et al. | |
| 8,304,253 B2 | 11/2012 | Yi et al. | |
| 8,313,698 B2 | 11/2012 | Pollack et al. | |
| 8,317,990 B2 | 11/2012 | Pamula et al. | |
| 8,342,207 B2 | 1/2013 | Raccurt et al. | |
| 8,349,276 B2 | 1/2013 | Pamula et al. | |
| 8,364,315 B2 | 1/2013 | Sturmer et al. | |
| 8,388,909 B2 | 3/2013 | Pollack et al. | |
| 8,389,297 B2 | 3/2013 | Pamula et al. | |
| 8,394,249 B2 | 3/2013 | Pollack et al. | |
| 8,394,641 B2 | 3/2013 | Winger | |
| 8,426,213 B2 | 4/2013 | Eckhardt et al. | |
| 8,440,392 B2 | 5/2013 | Pamula et al. | |
| 8,444,836 B2 | 5/2013 | Fouillet et al. | |
| 2002/0005354 A1 | 1/2002 | Spence et al. | |
| 2002/0036139 A1 | 3/2002 | Becker et al. | |
| 2002/0043463 A1 | 4/2002 | Shenderov | |
| 2002/0058332 A1 | 5/2002 | Quake et al. | |
| 2002/0143437 A1 | 10/2002 | Handique et al. | |
| 2003/0164295 A1 | 9/2003 | Sterling | |
| 2003/0183525 A1 | 10/2003 | Elrod et al. | |
| 2003/0205632 A1 | 11/2003 | Kim et al. | |
| 2004/0031688 A1 | 2/2004 | Shenderov | |
| 2004/0055891 A1 | 3/2004 | Pamula et al. | |
| 2004/0058450 A1 | 3/2004 | Pamula et al. | |
| 2004/0231987 A1 | 11/2004 | Sterling et al. | |
| 2006/0021875 A1 | 2/2006 | Griffith et al. | |
| 2006/0054503 A1 | 3/2006 | Pamula et al. | |
| 2006/0102477 A1* | 5/2006 | Vann et al. | 204/450 |
| 2006/0164490 A1 | 7/2006 | Kim et al. | |
| 2006/0194331 A1 | 8/2006 | Pamula et al. | |
| 2006/0226012 A1* | 10/2006 | Kanagasabapathi et al. | 204/547 |
| 2006/0231398 A1 | 10/2006 | Sarrut et al. | |
| 2007/0023292 A1 | 2/2007 | Kim et al. | |
| 2007/0037294 A1 | 2/2007 | Pamula et al. | |
| 2007/0045117 A1 | 3/2007 | Pamula et al. | |
| 2007/0064990 A1 | 3/2007 | Roth | |
| 2007/0086927 A1 | 4/2007 | Natarajan et al. | |
| 2007/0207513 A1 | 9/2007 | Sorensen et al. | |
| 2007/0217956 A1 | 9/2007 | Pamula et al. | |
| 2007/0241068 A1 | 10/2007 | Pamula et al. | |
| 2007/0242105 A1 | 10/2007 | Srinivasan et al. | |
| 2007/0242111 A1 | 10/2007 | Pamula et al. | |
| 2007/0243634 A1 | 10/2007 | Pamula et al. | |
| 2007/0267294 A1 | 11/2007 | Shenderov | |
| 2007/0275415 A1 | 11/2007 | Srinivasan et al. | |
| 2008/0006535 A1 | 1/2008 | Paik et al. | |
| 2008/0038810 A1 | 2/2008 | Pollack et al. | |
| 2008/0044893 A1 | 2/2008 | Pollack et al. | |
| 2008/0044914 A1 | 2/2008 | Pamula et al. | |
| 2008/0050834 A1 | 2/2008 | Pamula et al. | |
| 2008/0053205 A1 | 3/2008 | Pollack et al. | |
| 2008/0105549 A1 | 5/2008 | Pamela et al. | |
| 2008/0124252 A1 | 5/2008 | Marchand et al. | |
| 2008/0142376 A1 | 6/2008 | Fouillet et al. | |
| 2008/0151240 A1 | 6/2008 | Roth | |
| 2008/0166793 A1* | 7/2008 | Beer et al. | 435/287.2 |
| 2008/0210558 A1 | 9/2008 | Sauter-Starace et al. | |
| 2008/0247920 A1 | 10/2008 | Pollack et al. | |
| 2008/0264797 A1 | 10/2008 | Pamula et al. | |
| 2008/0274513 A1 | 11/2008 | Shenderov et al. | |
| 2008/0281471 A1 | 11/2008 | Smith et al. | |
| 2008/0283414 A1 | 11/2008 | Monroe et al. | |
| 2008/0302431 A1 | 12/2008 | Marchand et al. | |
| 2008/0305481 A1 | 12/2008 | Whitman et al. | |
| 2009/0014394 A1 | 1/2009 | Yi et al. | |
| 2009/0042319 A1 | 2/2009 | De Guzman et al. | |
| 2009/0127123 A1 | 5/2009 | Raccurt et al. | |
| 2009/0134027 A1 | 5/2009 | Jary | |
| 2009/0142564 A1 | 6/2009 | Plissonier et al. | |
| 2009/0155902 A1 | 6/2009 | Pollack et al. | |
| 2009/0192044 A1 | 7/2009 | Fouillet | |
| 2009/0260988 A1 | 10/2009 | Pamula et al. | |
| 2009/0263834 A1 | 10/2009 | Sista et al. | |
| 2009/0280251 A1 | 11/2009 | De Guzman et al. | |
| 2009/0280475 A1 | 11/2009 | Pollack et al. | |
| 2009/0280476 A1 | 11/2009 | Srinivasan et al. | |
| 2009/0283407 A1 | 11/2009 | Shah et al. | |
| 2009/0288710 A1 | 11/2009 | Viovy et al. | |
| 2009/0291433 A1 | 11/2009 | Pollack et al. | |
| 2009/0304944 A1 | 12/2009 | Sudarsan et al. | |
| 2009/0311713 A1 | 12/2009 | Pollack et al. | |
| 2009/0321262 A1 | 12/2009 | Adachi et al. | |
| 2010/0025242 A1 | 2/2010 | Pamula et al. | |
| 2010/0025250 A1 | 2/2010 | Pamula et al. | |
| 2010/0028920 A1 | 2/2010 | Eckhardt | |
| 2010/0032293 A1 | 2/2010 | Pollack et al. | |
| 2010/0041086 A1 | 2/2010 | Pamula et al. | |
| 2010/0048410 A1 | 2/2010 | Shenderov et al. | |
| 2010/0062508 A1 | 3/2010 | Pamula et al. | |

(56) References Cited

U.S. PATENT DOCUMENTS

| | | |
|---|---|---|
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0059366 A1 | 3/2013 | Pollack et al. |

FOREIGN PATENT DOCUMENTS

| | | | |
|---|---|---|---|
| WO | 0069565 | A1 | 11/2000 |
| WO | 0073655 | A1 | 12/2000 |
| WO | 2004029585 | A1 | 4/2004 |
| WO | 2004030820 | | 4/2004 |
| WO | 2005047696 | A1 | 5/2005 |
| WO | 2006013303 | A1 | 2/2006 |
| WO | 2006070162 | A1 | 7/2006 |
| WO | 2006081558 | | 8/2006 |
| WO | 2006124458 | A2 | 11/2006 |
| WO | 2006127451 | A2 | 11/2006 |
| WO | 2006134307 | A1 | 12/2006 |
| WO | 2006138543 | | 12/2006 |
| WO | 2007003720 | A1 | 1/2007 |
| WO | 2007012638 | A1 | 2/2007 |
| WO | 2007033990 | A1 | 3/2007 |
| WO | 2007048111 | | 4/2007 |
| WO | 2007120240 | A2 | 10/2007 |
| WO | 2007120241 | A2 | 10/2007 |
| WO | 2007123908 | A2 | 11/2007 |
| WO | 2008051310 | A2 | 5/2008 |
| WO | 2008055256 | A3 | 5/2008 |
| WO | 2008068229 | A1 | 6/2008 |
| WO | 2008091848 | A2 | 7/2008 |
| WO | 2008098236 | A2 | 8/2008 |
| WO | 2008101194 | A2 | 8/2008 |
| WO | 2008106678 | A1 | 9/2008 |
| WO | 2008109664 | A1 | 9/2008 |
| WO | 2008112856 | A1 | 9/2008 |
| WO | 2008116209 | A1 | 9/2008 |
| WO | 2008116221 | A1 | 9/2008 |
| WO | 2008118831 | A2 | 10/2008 |
| WO | 2008124846 | A2 | 10/2008 |
| WO | 2008131420 | A2 | 10/2008 |
| WO | 2008134153 | A1 | 11/2008 |
| WO | 2009002920 | A1 | 12/2008 |
| WO | 2009003184 | A1 | 12/2008 |
| WO | 2009011952 | A1 | 1/2009 |
| WO | 2009021173 | A1 | 2/2009 |
| WO | 2009021233 | A2 | 2/2009 |
| WO | 2009026339 | A2 | 2/2009 |
| WO | 2009029561 | A2 | 3/2009 |
| WO | 2009032863 | A2 | 3/2009 |
| WO | 2009052095 | A1 | 4/2009 |
| WO | 2009052123 | A2 | 4/2009 |
| WO | 2009052321 | A2 | 4/2009 |
| WO | 2009052345 | A1 | 4/2009 |
| WO | 2009052348 | A2 | 4/2009 |
| WO | 2009076414 | | 6/2009 |
| WO | 2009086403 | A2 | 7/2009 |
| WO | 2009111769 | A2 | 9/2009 |
| WO | 2009135205 | A2 | 11/2009 |
| WO | 2009137415 | A2 | 11/2009 |
| WO | 2009140373 | A2 | 11/2009 |
| WO | 2009140671 | A2 | 11/2009 |
| WO | 2010004014 | A1 | 1/2010 |
| WO | 2010006166 | A2 | 1/2010 |
| WO | 2010009463 | A2 | 1/2010 |
| WO | 2010019782 | A2 | 2/2010 |
| WO | 2010027894 | A2 | 3/2010 |
| WO | 2010042637 | A2 | 4/2010 |
| WO | 2010077859 | A3 | 7/2010 |
| WO | 2011002957 | A2 | 1/2011 |
| WO | 2011020011 | A2 | 2/2011 |
| WO | 2011057197 | A2 | 5/2011 |
| WO | 2011084703 | A2 | 7/2011 |
| WO | 2011126892 | A2 | 10/2011 |
| WO | 2012009320 | A2 | 1/2012 |
| WO | 2012012090 | A2 | 1/2012 |
| WO | 2012037308 | A2 | 3/2012 |

OTHER PUBLICATIONS

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

Cotten et al., "Digital Microfluidics: a novel platform for multiplexed detection of lysosomal storage diseases", Abstract # 3747.9. Pediatric Academic Society Conference, 2008.

Delattre, Movie in news on TF1 (at 12'45" Cyril Delattre), http://videos.tf1.fr/jt-we/zoom-sur-grenoble-6071525.html, 2009.

Delattre, Movie in talk show "C Dans l'air" (at 24" Cyril Delattre), http://www.france5.fr/c-dans-l-air/sante/bientot-vous-ne-serez-plus-malade-31721, 2009.

(56) References Cited

OTHER PUBLICATIONS

Delattre, Movie on Web TV—Cite des sciences (at 3'26" Cyril Delattre), http://www.universcience.tv/video-laboratoire-de-poche-793.html, 2009.
Delattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.
Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.
Delattre et al., "Towards an industrial fabrication process for electrowetting chip using standard MEMS Technology", µTAS2008, San Diego; poster presented, Oct. 15, 2008.
Delattre et al., "Towards an industrial fabrication process for electrowetting chip using standard MEMS Technology", µTAS2008, San Diego; Abstract in proceedings, Oct. 13-16, 2008, 1696-1698.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Emani et al., "Novel Microfluidic Platform for Point of Care Hypercoagulability Panel Testing", Circulation, vol. 122, 2010, A14693.
Fair et al., "A Micro-Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Workshop, Rochester, NY, May 31, 2006.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fair et al., "Integrated chemical/biochemical sample collection, preconcentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.
Fair, "Scaling of Digital Microfluidic Devices for Picoliter Applications", The 6th International Electrowetting Meeting, Aug. 20-22, 2008, p. 14.
Fouillet, "Bio-Protocol Integration in Digital Microfluidic Chips", The 6th International Electrowetting Meeting, Aug. 20-22, 2008, p. 15.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Fouillet et al., "Digital microfluidic design and optimization of classic and new fluidic functions for lab on a chip systems", Microfluid Nanofluid, vol. 4, 2008, 159-165.

Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.
Hua et al., "Rapid Detection of Methicillin-Resistant Staphylococcus Aureus (MRSA) Using Digital Microfluidics", 12th Intl Conference on Miniaturized Systems for Chemistry and Life Sciences, Proc. µTAS, Oct. 12-16, 2008.
Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.
Jary et al., "SmartDrop, Microfluidics for Biology", Forum 4i 2009, Grenoble, France; Flyer distributed at booth, May 14, 2009.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.
Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.
Kleinert, "Electric-Field-Assisted Convective Assembly of Colloidal Crystal Coatings", Langmuir, vol. 26(12), May 13, 2010, 10380-10385.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.
Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal
&id=ASMECP002010054501000023900000, Aug. 1-5, 2010.
Marchand et al., "Organic Synthesis in Soft Wall-Free Microreactors: Real-Time Monitoring of Fluorogenic Reactions", Analytical Chemistry, vol. 80, Jul. 2, 2008, 6051-6055.
Millington et al., "Digital microfluidics: a future technology in the newborn screening laboratory", Seminars in Perinatology, vol. 34, Apr. 2010, 163-169.
Millington et al., "Digital Microfluidics: a novel platform for multiplexed detection of LSDs with potential for newborn screening", Association of Public Health Laboratories Annual Conference, San Antonio, TX, Nov. 4, 2008.
Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.
Paik et al., "A digital-microfluidic approach to chip cooling", IEEE Design & Test of Computers, vol. 25, Jul. 2008, 372-381.

(56) References Cited

OTHER PUBLICATIONS

Paik et al., "Adaptive Cooling of Integrated Circuits Using Digital Microfluidics", IEEE Transactions on VLSI, vol. 16, No. 4, 2008, 432-443.
Paik et al., "Adaptive Cooling of Integrated Circuits Using Digital Microfluidics", accepted for publication in IEEE Transactions on VLSI Systems, 2007, and Artech House, Norwood, MA, 2007.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.
Paik et al., "Programmable flow-through real-time PCR using digital microfluidics", Proc. Micro Total Analysis Systems (μTAS), Handout, 2007.
Paik et al., "Programmable flow-through real-time PCR using digital microfluidics", Proc. Micro Total Analysis Systems (μTAS), Poster, 2007.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3. (More mixing videos available, along with the article, at LOC's website.), 2003, 253-259.
Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula, "Digital microfluidic lab-on-a-chip for multiplexing tests in newborn screening", Newborn Screening Summit: Envisioning a Future for Newborn Screening, Bethesda, MD, Dec. 7, 2009.
Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.
Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula, "Sample Preparation and Processing using Magnetic Beads on a Digital Microfluidic Platform", CHI's Genomic Sample Prep, San Francisco, CA, Jun. 9-10, 2009.
Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.
Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.
Pollack, et al., "Electrowetting-Based Actuation of Droplets for Integrated Microfluidics", Lab on a Chip (LOC), vol. 2, 2002, 96-101.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Pollack, "Lab-on-a-chip platform based digital microfluidics", The 6th International Electrowetting Meeting, Aug. 20-22, 2008, 16.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.
Rival et al., "Expression de gènes de quelques cellules sur puce EWOD/Gene expression of few cells on EWOD chip", iRTSV,http://www-dsv.cea.fr/var/plain/storage/original/media/File/iRTSV/thema__08(2).pdf (english translation), Winter 2009-2010.
Rival et al., "Towards Single Cells Gene Expression on EWOD Lab on Chip", ESONN 2008, Grenoble, France; Poster presented, Aug. 26, 2008.
Rival et al., "Towards single cells gene expression on EWOD lab on chip", ESONN, Grenoble, France, abstract in proceedings, Aug. 2008.
Rival et al., "Towards single cells gene expression preparation and analysis on ewod lab on chip", Nanobio Europe 2009, Poster distributed at conference, Jun. 16-18, 2009.
Rival et al., "Towards single cells gene expression preparation and analysis on ewod lab on chip", Nanobio Europe 2009, Abstract in proceedings, Jun. 16-18, 2009.
Rival et al., "Towards single cells gene expression preparation and analysis on ewod lab on chip", Lab on Chip Europe 2009 poster distributed at Conference, May 19-20, 2009.

(56) References Cited

OTHER PUBLICATIONS

Rival et al., "Towards single cells gene expression preparation and analysis on ewod lab on chip", Lab on Chip Europe 2009, Abstract in proceedings, May 19-20, 2009.

Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.

Sherman et al., "Flow Control by Using High-Aspect-Ratio, In-Plane Microactuators", Sensors and Actuators, vol. 73, 1999, pp. 169-175.

Sherman et al., "In-Plane Microactuator for Fluid Control Application", Proc. IEEE Micro Electro Mechanical Systems Workshop, Heidelberg, Germany, Jan. 1998, pp. 454-459.

Sista et al., "96-Immunoassay Digital Microfluidic Multiwell Plate", Proc. µTAS, Oct. 12-16, 2008.

Sista, "Development of a Digital Microfluidic Lab-on-a-Chip for Automated Immunoassays with Magnetically Responsive Beads", PhD Thesis, Department of Chemical Engineering, Florida State University, 2007.

Sista et al., "Development of a digital microfluidic platform for point of care testing", Lab on a chip, vol. 8, Dec. 2008, First published as an Advance Article on the web, Nov. 5, 2008, 2091-2104.

Sista et al., "Digital Microfluidic platform for multiplexing LSD assays in newborn screening", APHL Newborn Screening and Genetic Testing Symposium, Orlando, May 3-6, 2010.

Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.

Sista et al., "Spatial multiplexing of immunoassays for small-volume samples", 10th PI Meeting IMAT, Bethesda, 2009.

Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.

Srinivasan et al., "A digital microfluidic biosensor for multianalyte detection", Proc. IEEE 16th Annual Int'l Conf. on Micro Electro Mechanical Systems Conference, 2003, 327-330.

Srinivasan, "A Digital Microfluidic Lab-on-a-Chip for Clinical Diagnostic Applications", Ph.D. thesis, Dept of Electrical and Computer Engineering, Duke University, 2005.

Srinivasan et al., "An integrated digital microfluidic lab-on-a-chip for clinical diagnostics on human physiological fluids", Lab on a Chip, vol. 4, 2004, 310-315.

Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.

Srinivasan et al., "Digital Microfluidic Lab-on-a-Chip for Protein Crystallization", The 82nd ACS Colloid and Surface Science Symposium, 2008.

Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.

Srinivasan et al., "Droplet-based microfluidic lab-on-a-chip for glucose detection", Analytica Chimica Acta, vol. 507, No. 1, 2004, 145-150.

Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.

Srinivasan et al., "Low cost digital microfluidic platform for protein crystallization", Enabling Technologies for Structural Biology, NIGMS Workshop, Bethesda, MD., Mar. 4-6, 2009, J-23.

Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Srinivasan et al., "Scalable Macromodels for Microelectromechanical Systems", Technical Proc. 2001 Int. Conf. on Modeling and Simulation of Microsystems, 2001, 72-75.

Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published on-line, May 2004, 3229-3235.

Thwar et al., "DNA sequencing using digital microfluidics", Poster 42, 41st AACC's Annual Oak Ridge Conference Abstracts, Clinical Chemistry vol. 55, 2009, 1891.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Wulff-Burchfield et al., "Microfluidic platform versus conventional real-time polymerase chain reaction for the detection of Mycoplasma pneumoniae in respiratory specimens", Diagnostic Microbiology and Infectious Disease, vol. 67, 2010, 22-29.

Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Defect-Tolerant Design and Optimization of a Digital Microfluidic Biochip for Protein Crystallization", IEEE Transactions on Computer Aided Design, vol. 29, No. 4, 2010, 552-565.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, LISA, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", CODES, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yang et al., "Manipulation of droplets in microfluidic systems", Trends in Analytical Chemistry, vol. 29, Feb. 2010, 141-157.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16., Oct. 2006, 2053-2059.

(56) References Cited

OTHER PUBLICATIONS

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

Zhao et al., "Synchronization of Concurrently-Implemented Fluidic Operations in Pin-Constrained Digital Microfluidic Biochips", VLSI Design, (Best Paper Award), 2010.

International Search Report dated Aug. 2, 2011 from PCT International Application No. PCT/US2010/055843.

* cited by examiner

INTEGRATED DROPLET ACTUATOR FOR GEL; ELECTROPHORESIS AND MOLECULAR ANALYSIS

1 RELATED APPLICATIONS

In addition to the patent applications cited herein, each of which is incorporated herein by reference, this patent application is related to and claims priority to U.S. Provisional patent application No. 61/258,827, filed on Nov. 6, 2009, entitled "Integrated Droplet Actuator for Gel Electrophoresis and Molecular Analysis", the entire disclosure of which are incorporated herein by reference.

2 FIELD OF THE INVENTION

The invention generally relates to an integrated droplet actuator device and techniques. In particular, the invention is directed to an integrated droplet actuator device and techniques for gel electrophoresis and molecular analysis.

3 BACKGROUND

Droplet actuators are used to conduct a wide variety of droplet operations. A droplet actuator typically includes one or more substrates configured to form a surface or gap for conducting droplet operations. The one or more substrates include electrodes for conducting droplet operations. The gap between the substrates is typically filled or coated with a filler fluid that is immiscible with the liquid that is to be subjected to droplet operations. Droplet operations are controlled by electrodes associated with the one or more substrates.

Droplet actuators are used in a variety of analytical settings, such as biomedical research and clinical diagnostics. Depending on the type of analysis performed, one or more different molecular techniques are often implemented together, providing a wide range of field-specific applications. Many of the molecular techniques typically used to analyze a biological sample, such as a DNA sample, are often implemented in conjunction with gel electrophoresis. Gel electrophoresis is a technique routinely used to separate nucleic acids (and other biological molecules) based on size. In one example, gel electrophoresis may be used to assess the quality (e.g., measured as a function of average fragment size) of a DNA sample prior to more complex analysis such as genotyping. In another example, gel electrophoresis may be used to analyze specific DNA restriction enzyme digestion patterns or polymerase chain reaction (PCR) amplification fragments. Specific DNA bands may also be isolated from a gel matrix for subsequent manipulations, such as cloning or sequencing. However, this approach of combined analyses is labor-intensive and expensive because it requires each technique to be performed separately and often sequentially. There is a need for improved methods for implementing one or more molecular techniques that provides for flexibility in assay design and for comprehensive sample handling and analysis.

4 SUMMARY OF THE INVENTION

The invention is directed to an integrated droplet actuator device and techniques for gel electrophoresis and molecular analysis.

In one embodiment, the invention provides an integrated droplet actuator device including a top substrate and a bottom substrate; the two substrates configure to form a droplet operations gap. The integrated droplet actuator device may further include electrodes associated with one or both of the bottom substrate and the top substrate, and configured for conducting droplet operations in the gap; a gel arranged on the top substrate; a pair of electrodes in electrical contact with the gel, the electrodes arranged at first and second locations in relation to the gel; and one or more fluid paths extending from inside the gap to the gel.

In another embodiment, the invention provides a method of preparing and delivering a sample droplet for gel electrophoresis in an integrated droplet actuator device. The method preferably includes providing an integrated droplet actuator device, including a top substrate and a bottom substrate, where the two substrates are configured to form a droplet operations gap; electrodes associated with one or both of the bottom substrate and the top substrate, and configured for conducting droplet operations in the gap; a gel arranged on the top substrate; a pair of electrodes in electrical contact with the gel, the electrodes arranged at first and second locations in relation to the gel; and one or more fluid paths extending from inside the gap to the gel. The method may further include loading a droplet containing a sample material on at least one of the one or more electrodes, where at least one electrode is in proximity to the one or more fluid paths; transferring the sample material into a loading buffer; and transferring the sample material from the loading buffer into the gel. The method may further include concentrating the sample material include delivering, using droplet operations, additional droplets containing the sample material to at least one of the one or more electrodes in proximity to the one or more fluid paths; and transferring the sample material, from the additional droplets, into the loading buffer until a desired concentration of sample material is achieved.

In yet another embodiment, the invention provides a method of preparing and delivering a sample droplet for gel eletrophoresis in an integrated droplet actuated device. The method preferably includes providing an integrated droplet actuated device, including a top substrate and a bottom substrate, the two substrates configured to form a droplet operations gap; electrodes associated with one or both of the bottom substrate and the top substrate, and configured for conducting droplet operations in the gap; a gel arranged on the top substrate, wherein at least a portion of the gel extends into the gap of the integrated droplet actuator; a pair of electrodes in electrical contact with the gel, the electrodes arranged at first and second locations in relation to the gel; and one or more fluid paths extending from inside the gap to the gel. The method may further include loading a droplet containing a sample material on at least one of the one or more electrodes, where the at least one electrode is in proximity to the one or more fluid paths; transferring the sample material into a loading buffer retained in the one or more fluid paths; and transferring the sample material from the loading buffer into the gel. The method may further include concentrating the sample material include delivering, using droplet operations, additional droplets containing the sample material to at least one of the one or more electrodes in proximity to the one or more fluid paths; and transferring the sample material, from the additional droplets, into the loading buffer until a desired concentration of sample material is achieved.

In still yet another embodiment, the intervention provides an integrated droplet actuator device for conducting molecular assays, including a top substrate and a bottom substrate, the two substrates configured to form a droplet operations gap; electrodes associated with one or both of the bottom substrate, and configure for conducting droplet operations in the gap; a gel arranged on the top sub straight; a pair of electrodes in electrical contact with the gel, the electrodes arranged at first and second locations in relation to the gel; one or more fluid paths extending from inside the gap to the gel; and at least a first reaction zone and a second reaction zone.

In still yet another embodiment, the invention provides a method of conducting a molecular analysis and integrated droplet actuator device. The method may include providing an integrated droplet actuator device for conducting molecular analysis, including a top substrate and a bottom substrate, the two substrates configured to form a droplet operations gap; electrodes associated with one or both of the bottom substrate and the top substrate, and configure for conducting droplet operations in the gap; a gel arranged on the top substrate; a pair of electrodes in electrical contact with the gel, the electrodes arranged at first and second locations in relation to the gel; one or more fluid paths extending from inside the gap to the gel; and at least a first reaction zone and second reaction zone. The method may further include positioning a reaction droplet on an electrode in a first reaction zone and incubating the reaction droplet in the first reaction zone for a period of time; transporting the reaction droplet to the second reaction zone and incubating the reaction droplet in the second reaction zone for a period of time; and cycling the reaction droplet between at least the first reaction zone and at least the second reaction zone until a desired result is achieved.

In still yet another embodiment, the invention provides an electrode configuration for real-time PCR on a multi-channel integrated droplet actuator device. The device may include controlled electrode loops configured for conducting droplet operations arranged on a substrate of the integrated droplet actuator device, wherein each of the controlled electrode loops have at least a first reaction zone and a second reaction zone; and reservoir wells in fluidic connection with the controlled electrode loops, where the reservoir wells are adapted to dispense sample droplets on one or more electrodes of the controlled electrode loops.

In still yet another embodiment, the invention provides a method of conducting real-time PCR in a multi-channel integrated droplet actuated device. The method may include, dispensing a sample droplet containing a quantity of sample material from a first reservoir onto one or more electrodes of a controlled electrode loop arranged on a substrate of the integrated droplet actuator device; dispensing a PCR reagent sample droplet from a second reservoir onto one or more electrodes of a controlled electrode loop arranged on a substrate of the integrated droplet actuator device; merging and mixing the sample droplet and the PCR reagent sample droplet to form a combined droplet, thermocycling the combined droplet between at least two temperature zones positioned on the controlled electrode loop; and detecting a quantity of amplified sample material within the combined droplet.

In still yet another embodiment, the invention provides a method of diluting a sample in an integrated droplet actuator. The method may include dispensing a droplet containing sample material on one or more substrates of an integrated droplet actuator; merging the droplet with a buffer droplet and mixing to form a combined droplet; splitting the combined droplet into two essentially equal diluted droplets; and repeating until a value within a range sufficient for sample analysis is achieved.

In still yet another embodiment, the invention provides a method of conducting multiple assays on an integrated droplet actuator. The method may include providing an integrated droplet actuator having one or more reagent reservoirs, at least one sample reservoir, and an electrophoresis gel; dispensing an initial sample droplet comprising a quantity of sample material from the at least one sample reservoir onto a substrate of the integrated droplet actuator; quantitating the concentration of the sample material in the dispensed initial sample droplet; determining, using the total quantified sample material concentration, a sample droplet volume having an appropriate amount of sample material required for conducting gel electrophoresis; dispensing the required sample droplet volume from the at least one sample reservoir onto the substrate of the integrated droplet actuator; transporting the required sample droplet volume to the electrophoresis gel and conducting electrophoresis-based assay; dispensing another sample droplet from the at least one sample reservoir onto the substrate of the integrated droplet actuator and mixing with a reagents droplet dispensed from the one or more reagents reservoir to form a combined droplet; and analyzing the combined droplet and a sample material standard droplet having a known sample material quantity, to determine the quantity of sample material present in the sample. Quantitating may include merging and mixing a sample droplet with a droplet comprising a quantitation reagent to form a combined droplet; measuring the florescence of the combined droplet; merging and mixing a standard droplet having a known sample material concentration with a droplet comprising a quantitation reagent to form a combined standard droplet; measuring florescence of the standard droplet and of the combined standard droplet; and comparing the florescence of the combined droplet with the florescence of the combined standard droplet to determine the sample material concentration and the sample droplet.

5 DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Corp., Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication No. 20050260686, entitled, "Multiplex flow assays preferably with magnetic particles as solid phase," published on Nov. 24, 2005, the entire disclosure of which is incorporated herein by reference for its teaching concerning magnetically responsive materials and beads. Beads may be pre-coupled with a biomolecule (ligand). The ligand may, for example, be an antibody, protein or antigen, DNA/RNA probe or any other molecule with an affinity for the desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. patent application No. 61/039,183, entitled "Multiplexing Bead Detection in a Single Droplet," filed on Mar, 25, 2008; U.S. patent application No. 61/047,789, entitled "Droplet Actuator Devices and Droplet Operations Using Beads," filed on Apr. 25, 2008; U.S. patent application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. 6,911, 132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling fluid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet;

cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

6 BRIEF DESCRIPTION OF THE DRAWINGS

7 DESCRIPTION

The present invention provides a droplet actuator device and methods for integrating gel electrophoresis analysis with pre or post-analytical sample handling as well as other molecular analysis processes. Using digital microfluidics technology, the droplet actuator device and methods of the invention provide the ability to perform gel electrophoresis and liquid handling operations on a single integrated device. The integrated liquid handling operations may be used to prepare and deliver samples to the electrophoresis gel, capture and subsequently process products of the electrophoresis gel or perform additional assays on the same sample materials which are analyzed by gel electrophoresis. In one embodiment, one or more molecular assays, such as nucleic acid (e.g., DNA) quantification by real-time PCR, and one or more sample processing operations such as sample dilution is performed on a droplet actuator integrated with an electrophoresis gel. In one embodiment, an electrophoresis gel slab may be integrated on the top substrate of the droplet actuator. In another embodiment, an electrophoresis gel slab may be integrated inside a microfluidic droplet actuator within an oil environment.

Because of the software programmability of digital microfluidics, essentially all of the parameters varied between and within different assay protocols, such as incubation times, sequences of reagent additions, washing protocols and thermal programs, may be configured on a single droplet actuator.

In one embodiment, the integrated microfluidic device may be used for DNA quality control testing.

7.1 Integration of Gel Electrophoresis on a Droplet actuator

Figure 1:
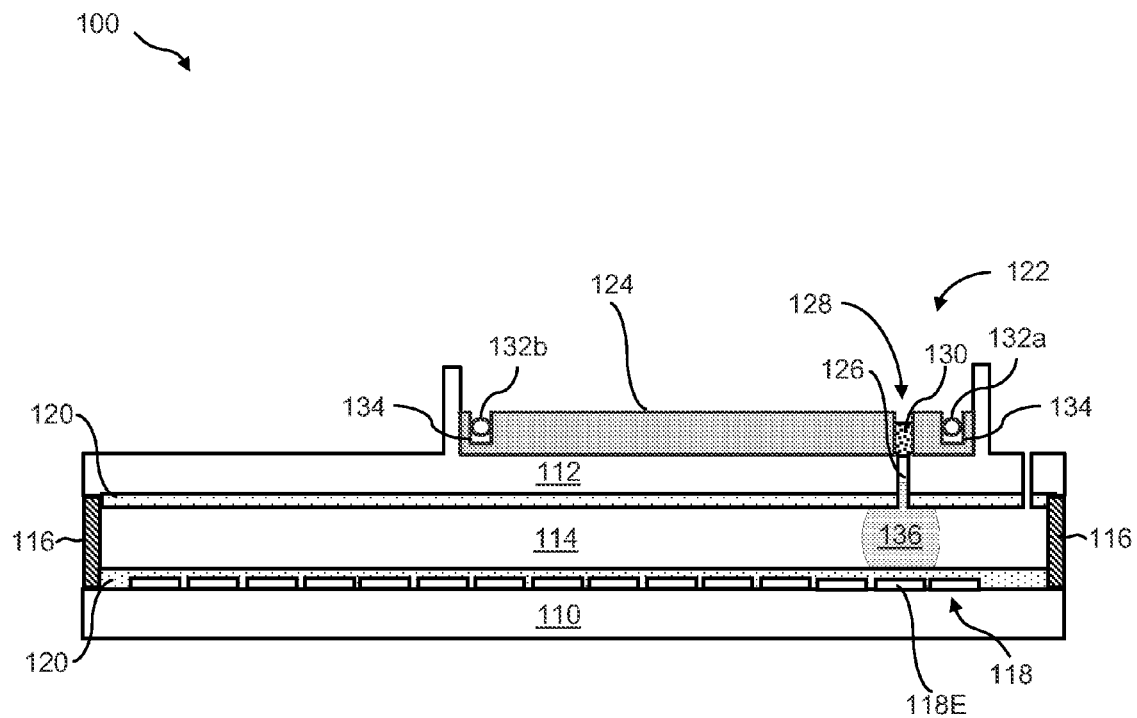
FIG. 1 illustrates a side view of a portion of an integrated droplet actuator for gel electrophoresis.

FIG. 1 illustrates a side view of a portion of an integrated droplet actuator 100 for gel electrophoresis. Integrated droplet actuator 100 of FIG. 1 is an example of a droplet actuator structure in which an electrophoresis gel slab is provided on the top substrate of the droplet actuator. The digital microfluidic layer and a gel electrophoresis layer are connected by through-holes fabricated in the top substrate of the droplet actuator.

Droplet actuator 100 may include a bottom substrate 110 and a top substrate 112 that are separated by a gap 114. Bottom substrate 110 may be attached to top substrate 112 by an epoxy glue ring 116. Gap 114 may be filled with a filler fluid, such as silicone oil (not shown).

Bottom substrate 110 may include a path or array of droplet operations electrodes 118 (e.g., electrowetting electrodes). Bottom substrate 110 may, for example, be formed of a printed circuit board (PCB). Top substrate 112 may, for example, be formed of a plastic material with high transparency and low fluorescence in the wavelength range compatible with fluorescence detection (i.e., suitable for fluorimeter operation). For example, top substrate 112 may be formed of cyclo-olefin polymer (COP) and/or copolymer (COC). A hydrophobic layer 120 may be disposed on the surface of bottom substrate 110 that is facing gap 114 (i.e., atop droplet operations electrodes 118). Similarly, another hydrophobic layer 120 may be disposed on the surface of top substrate 112 that is facing gap 114.

Top substrate 112 may include a protruded structure 122 of sufficient size to accommodate a gel slab 124 for electrophoresis (e.g., agarose gel electrophoresis). One or more openings 126 are provided within top substrate 112. Openings 126 in top substrate 112 provide a fluid path from certain droplet operations electrodes 118 (e.g., droplet operations electrode 118E) to one or more corresponding nucleic acid loading slots 128 that are molded into gel slab 124. Loading slots 128 may be partially filled with a loading buffer 130. Loading buffer 130 is retained in loading slot 128 by surface tension forces. The alignment of opening 126 and loading slot 128 is such that a microfluidics-gel interface is formed. A pair of thin wire electrodes 132 (e.g., electrode 132a and electrode 132b) may be positioned at two ends of gel slab 124 and parallel to loading slots 128. Electrodes 132 may be directly attached to and integrated with top substrate 112 or may be positioned in a trench 134 that is molded into gel slab 124. Trench 134 may be filled with an electrophoresis buffer (not shown), such as TBE. Trench 134 is an electrical interface that provides a uniform electrical field in gel slab 124. In another example, electrodes 132 may be embedded in gel slab 124. Electrodes 132 may, for example, be platinum wires. Electrodes 132 may be connected to an electrophoresis power supply (not shown). Electrode 132a may, for example, be a negative electrode (anode). Electrode 132b may, for example, be a positive electrode (cathode). In one embodiment, electrophoresis may be conducted without submerging gel slab 124 in an electrophoresis buffer (e.g., TBE). In another embodiment, gel slab 124 may be submerged in an electrophoresis buffer.

A droplet 136 may be positioned, for example, at droplet operations electrode 118E. Droplet 136 may, for example, be an aqueous sample droplet that contains a quantity of nucleic acid to be sized by gel electrophoresis. Droplet 136 on droplet operations electrode 118E is in proximity of the microfluidics-gel interface formed at opening 126 and loading slot 128. At this interface, a surface energy gradient may be formed from the hydrophobic droplet actuator inner space through the less hydrophobic opening 126, to the hydrophilic loading slot 128 in gel slab 124.

Because of the surface energy gradient formed at the interface, droplet 136 automatically flows upward due to capillary action and is merged into loading buffer 130 retained in loading slot 128. In another embodiment, the gel slab 124 extends into the interior of the droplet actuator avoiding the need to transport the droplet 136 through the opening 126. Alternatively, droplet 136 may remain inside the inner space but in contact with the loading buffer 130 through opening 126 so that material (e.g. DNA) can be transferred between the two spaces without bulk liquid transfer. In one embodiment, material is transferred between droplet 136 to loading buffer 130 through chemical diffusion. In another embodiment, material is transferred between droplet 136 to loading buffer 130 by electrophoresis. In this embodiment an electrical field gradient is established throughout the continuous liquid body formed by droplet 136 and loading buffer 130 connected through opening 126 which causes charged molecules to be concentrated in one end of the continuous liquid body. In any of these embodiments the transfer of material may occur in either direction, i.e. from the sample droplet 136 into loading buffer 130 or from loading buffer 130 into sample droplet 136. From the loading buffer 130 material may be transferred into the gel 124 by electrophoresis. Alternatively, gel electrophoresis products from gel 124 may be transferred into loading buffer 130. Thus, a means is provided both to deliver sample materials from the droplet actuator to the gel for analysis and to receive products of the gel analysis for subsequent processing on the droplet actuator.

7.2 Real-Time PCR on an Integrated Droplet actuator

Integrated droplet actuator 100 of FIG. 1 may be configured for one or more molecular assays. In one embodiment integrated droplet actuator 100 may be configured for real-time PCR.

Figure 2:
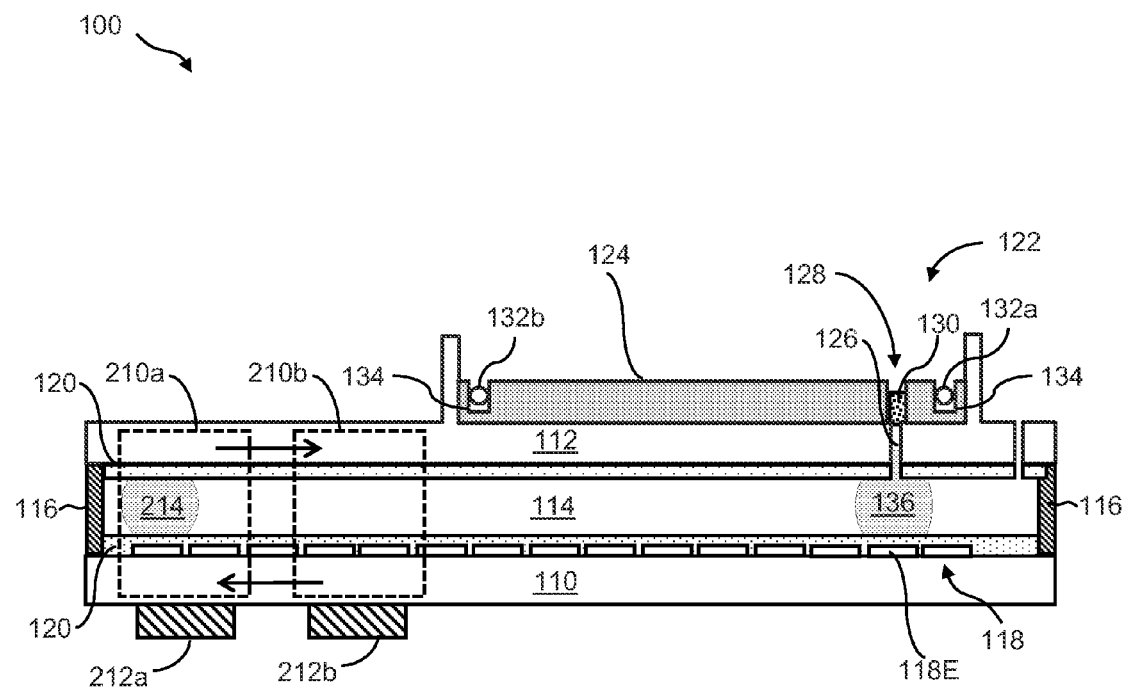
FIG. 2 illustrates a side view of a portion of the integrated droplet actuator of FIG. 1 that is configured for real-time PCR analysis.

FIG. 2 illustrates a side view of a portion of integrated droplet actuator 100 of FIG. 1 that is configured for real-time PCR analysis. In this embodiment, integrated droplet actuator 100 further includes, for example, two temperature control or reaction zones 210, such as temperature control zone 210a and 210b. A pair of heater bars 212, such as heater bars 212a and 212b, may be used to control the temperature of filler fluid in vicinity of thermal reaction zones 210a and 210b, respectively. Each heater bar 212 may be, for example, an aluminum heater bar equipped with heating resistors and thermistor. In one example, heater bar 212a may be used to heat temperature control zone 210a to about 95° C. (melting temperature), which is a temperature sufficient for denaturation of DNA template and primers. Heater bar 212b may be used to heat temperature control zone 210b to about 55° C. to 65° C., which is a temperature sufficient for annealing of primer to single-stranded DNA template and primer extension by DNA polymerase.

Temperature control zones 210a and 210b may be positioned at a sufficient distance from gel slab 124 that they do not affect the temperature inside the gel.

A PCR reaction droplet 214 may be positioned at a certain droplet operations electrode in temperature control zone 210a. Reaction droplet 214 includes the components required for PCR amplification of a target DNA template and fluorescence detection of amplified product (e.g., Eva Green). Reaction droplet 214 may be incubated within temperature control zone 210a for a period of time that is sufficient to dissociate the target DNA to free single stranded template and denature any primer-dimer pairs. Reaction droplet 214 may be transported using droplet operations along droplet operations electrodes 118 to temperature control zone 210b. Reaction droplet 214 may be incubated within temperature control zone 210b for a period of time that is sufficient for annealing of primers to the single stranded target DNA template and extension of the annealed primers by DNA polymerase. Reaction droplet 214 may be repeatedly transported between temperature control zones 210a and 210b any number of times sufficient for a desired level of DNA amplification. Because of the low thermal conductivity of bottom substrate 110 and top substrate 112, PCR thermocycling and gel electrophoresis may be executed simultaneously without overheating gel slab 124.

While a two temperature control zone is described herein, it is envisioned that multiple control zones (i.e., three or more) would be possible.

Figure 3:
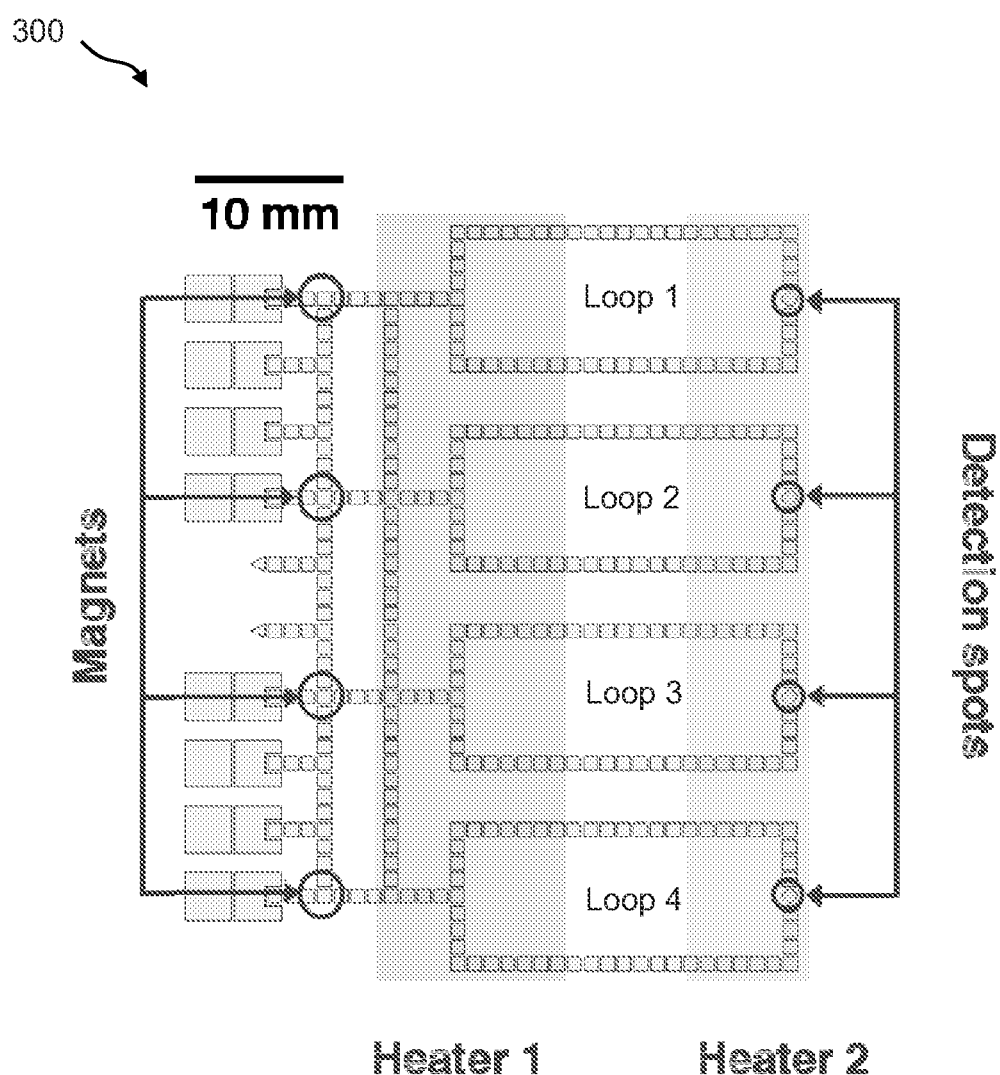
FIG. 3 illustrates a schematic diagram of an example of an electrode configuration for multi-channel real-time PCR on an integrated droplet actuator.

FIG. 3 illustrates a schematic diagram of an example of an electrode configuration 300 for multi-channel real-time PCR on an integrated droplet actuator. The PCR-integrated droplet actuator may include four independently controlled electrode loops (e.g., loops 1 through 4) as well as reservoirs for dispensing DNA samples and PCR reagents. Each thermocycler loop may circulate a single droplet or a droplet train between two temperature zones (e.g., between a 55-65° C. zone and a 95° C. zone). A detection spot may be provided within the 55-65° C. temperature zones in each thermocycler loop. For a typical PCR assay, a 300-nL droplet of DNA sample and a 300-nL droplet of PCR master mix and fluorescence dye (e.g., Eva Green) are dispensed from separate reservoirs and mixed using droplet operations. The combined droplet is then thermocycled between the two temperature zones. The amount of amplified DNA may be determined during each amplification cycle using a fluorimeter.

In one embodiment, a multi-channel real-time PCR assay may be used to assess the purity of a DNA sample. For example, a multiplexed PCR protocol may be used to quantitate the relative amounts of human DNA and non-human DNA (i.e. bacterial contamination) in a human biological sample (e.g., saliva). Contaminant DNA can be amplified and quantitated using primers pairs specific to particular common suspected bacterial contaminants (e.g., streptococcus, *Escherichia coli*), or by pooling multiple primers pairs each specific to a particular organism (i.e. multiplexed PCR) or by using primers which non-specifically amplify a broad class of organisms (i.e pan-bacterial or pan-fungal) by targeting highly-conserved sequences. Human DNA can be amplified and quantitated using primer pairs specific to particular human DNA sequences including many common reference genes. Relative quantitation of the human and non-human DNA present in a sample provides a means to assess the proportion of human DNA present in the total DNA sample. Alternatively, the amount of human or non-human DNA could be individually determined and compared to the amount of total DNA present in the sample (e.g. determined with Picogreen or Eva green fluorescent dye). Based on this quantitative assessment a sample may be rejected for further analysis if the contamination is determined to be unacceptable or the amount of total DNA used downstream may be adjusted to compensate for the presence of some fraction of non-human DNA. More generally, this approach can be used to quantitate the relative fraction of DNA contributed by any one organism or class or organisms within a mixed DNA sample (i.e. the sample need not be human and the contaminant need not be bacterial).

Sufficient sensitivity and specificity may be achieved by optimization of thermocycling conditions and PCR assay formulation. In particular, the type and concentration of the primer sets and polymerase, as well as the annealing temperature, may be chosen to selectively amplify human DNA in a bacterial DNA background or vice versa. The real-time detection may, for example, be by incorporation of a generic indicator, such as Eva Green. Alternatively, a specific indicator such as TaqMan probe or molecular beacon may be used to target specific sequences.

7.3 DNA Quantification on an Integrated Droplet actuator

In another embodiment, a serial dilution process and a DNA quantification assay may be combined on a droplet actuator, such as integrated droplet actuator 100 of FIG. 1 and/or FIG. 2. For example, a dilution protocol maybe applied prior to quantitation by a fluorescence assay, such as a PicoGreen™ assay if the undiluted sample is expected to be outside of the range of quantitation assay. Alternatively, if the undiluted sample is initially tested and found to be outside the range of the quantitation assay it may be diluted and retested. Alternatively, several different dilutions of the sample may be prepared initially and each one separately quantitated to provide several different values for each sample.

Dilution protocols may likewise be applied to a sample following the quantitation step. For example, a downstream process such as gel electrophoresis may require a particular concentration of DNA for optical performance. Based on the results on the quantitation step the sample may be diluted to achieve a particular amount or concentration in the sample droplet before being introduced into the gel. This could be performed on the same sample droplet analyzed in the quantitation step or, more likely on a separate aliquot from the same original sample.

In addition, a downstream process may require concentration rather than dilution to achieve a target amount or concentration of DNA. Concentration of DNA can generally be performed by several different methods on a droplet actuator including solid-phase capture and solvent evaporation. For gel electrophoresis, concentration can also be achieved by delivering multiple droplets to the loading well of the gel, i.e. the DNA contained in one or more droplets can be can combined in a well and "injected" as a single sample. Because of the substantially greater electrophoretic mobility of DNA in buffer compared to gel, the DNA within the loading well is effectively concentrated by electrophoresis.

Figure 4:
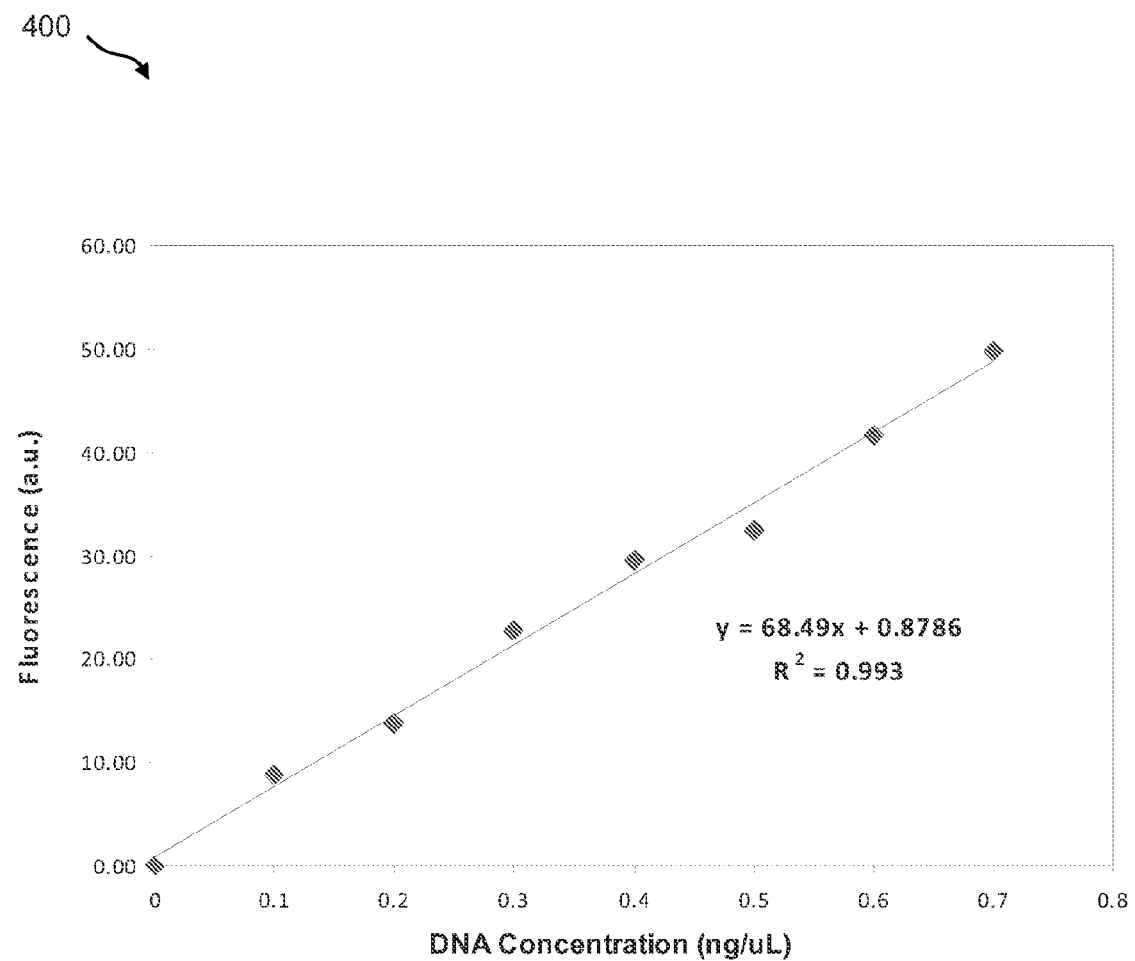
FIG. 4 shows a plot of fluorescence data of a DNA standard measured in a PicoGreen® assay.

FIG. 4 shows a plot 400 of fluorescence data of a DNA standard measured in a PicoGreen™ assay. A 500 ng/µL DNA sample was diluted off-chip to a series of concentrations ranging from 0.1 ng/µL to 0.7 ng/µL using TE buffer. A 300-nL droplet of each of the diluted DNA samples was dispensed and mixed with a 300-nL PicoGreen droplet. The fluorescence of the combined droplet was measured on a digital microfluidic chip using a fluorimeter. The data show a linear fluorescence response to the DNA concentrations between 0.1 and 0.7 ng/μL.

An on-chip binary dilution protocol may include, but is not limited to, the following steps:

In a first step, a 300-nL DNA sample droplet is merged and mixed using droplet operations with a 300-nL dilution buffer droplet (e.g., TE buffer) to yield a 600-nL combined droplet. In a second step, the 600-nL combined droplet is split into two identical 300-nL diluted droplets. In a third step, steps 1 and 2 are repeated on one of the diluted droplets formed in step 2. Steps 1 through 3 may be repeated any number of times (e.g., 1 to 10 times) sufficient for sample analysis.

Figure 5:
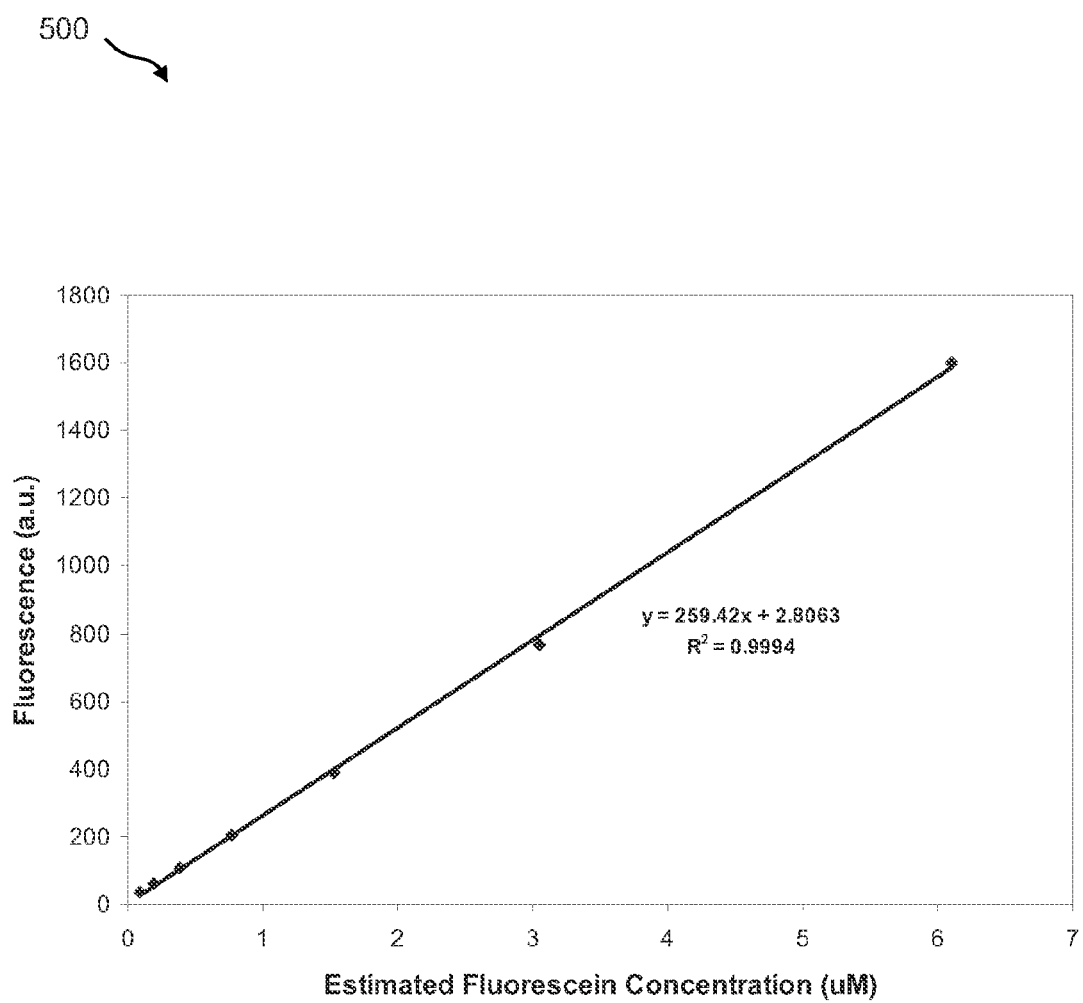
FIG. 5 shows a plot of fluorescence data from a binary dilution series performed on-chip.

Using fluoroscein tracer dye to demonstrate on-chip serial dilution because of its greater dynamic range, FIG. 5 shows a plot 500 of fluorescence data from a binary dilution series performed on-chip. The fluorescence of the dilution series was quantitated using a fluorimeter. The samples, from high concentration to low concentration, were transported sequentially to the same detection spot and measured using the same fluorimeter channel.

7.4 Fluorescence Detection

In one embodiment, a multi-channel, e.g., a four channel, fluorimeter module may be used for fluorescence detection on a droplet actuator, such as integrated droplet actuator 100 of FIG. 1 and/or FIG. 2. For example, one channel may be used for fluorescence detection of a DNA quantitation assay, such as a PicoGreen assay. The other three channels may be used for up to three real-time PCR reactions performed in parallel.

7.5 Example Application for an Integrated Droplet actuator

Because of the flexibility and programmability of the digital microfluidics platform, two or more different types of assays may be readily performed sequentially and/or simultaneously on a droplet actuator. In one embodiment, DNA quantification, multi-channel real-time PCR and gel electrophoresis may be performed on a single droplet actuator. For example, an integrated droplet actuator may be used to determine the quantity, quality (i.e., by sizing) and purity of one or more DNA samples, such as DNA samples provided through biobanks.

Figure 6:
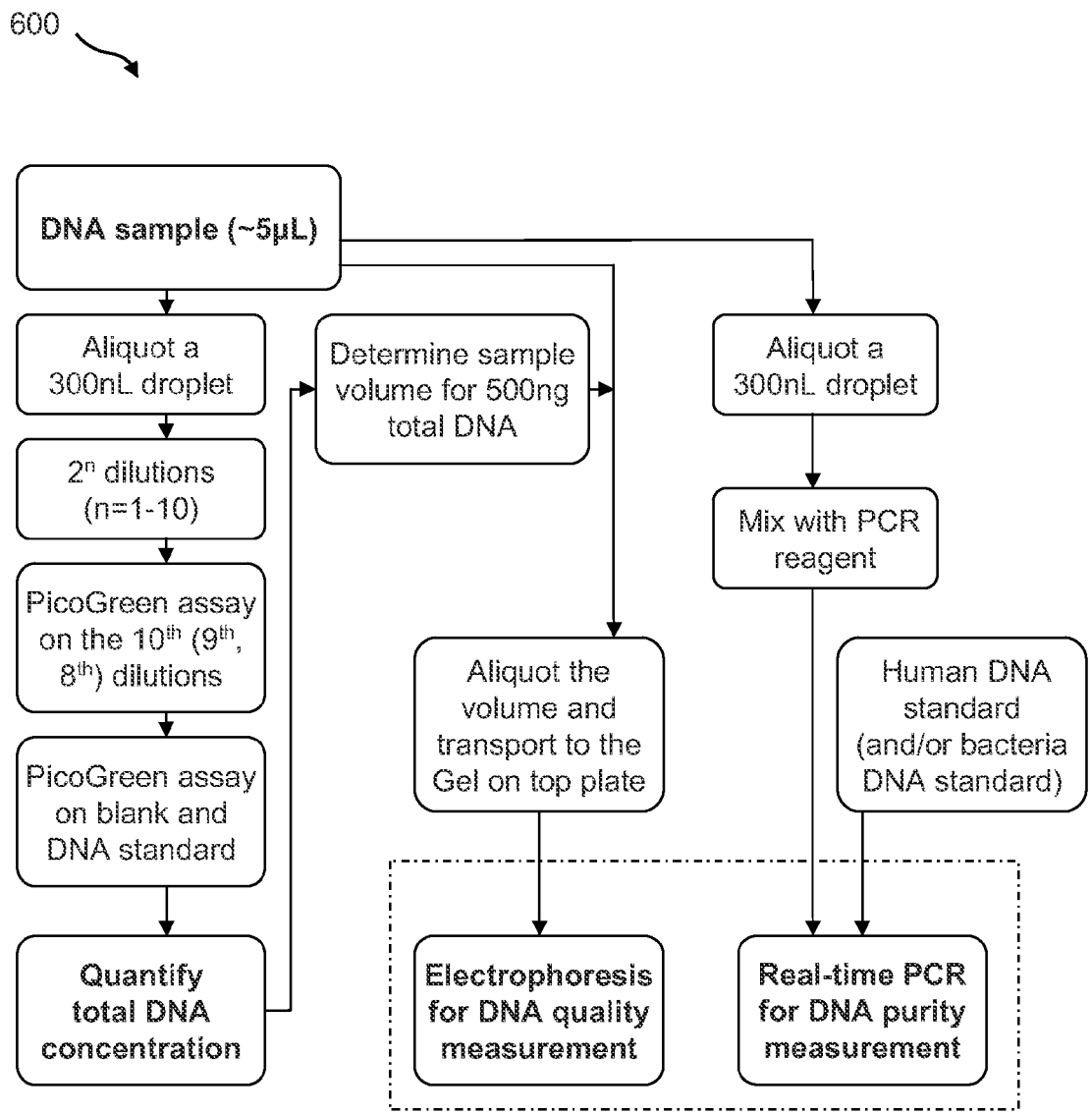
FIG. 6 illustrates a flow diagram of an example of a microfluidic protocol for multiplexed analysis of a DNA sample on an integrated droplet actuator.

FIG. 6 illustrates a flow diagram of an example of a microfluidic protocol 600 for multiplexed analysis of a DNA sample on an integrated droplet actuator. The integrated droplet actuator may be provided with reagent reservoirs that are loaded with dilution buffer (e.g., TE buffer), PicoGreen solution (for DNA quantitation), real-time PCR reagents, and/or a DNA standard (e.g., human DNA or bacterial DNA standard). A 5 μL aliquot of a DNA sample (e.g., a Biobank DNA sample) is loaded onto a sample reservoir of a droplet actuator.

In a first step, a 300-nL sample droplet is dispensed from the sample reservoir and serially diluted using, for example, a binary dilution protocol (e.g., $2^n$ where n=1-10).

In a second step, the $10^{th}$ (i.e., 1024-fold) dilution of the series, as well as the $10^{th}$ dilution of the DNA standard with known concentration is quantitated using a PicoGreen assay. A 300-nL droplet of the $10^{th}$ dilution of the DNA samples is mixed with a 300-nL 1X PicoGreen droplet, and the fluorescence measured using a fluorimeter. By comparing the fluorescence of the dilutions from the unknown DNA sample and the standard, the total DNA concentration in the original sample may be determined. Any variation in the dilution factor will not interfere with the quantification results. Optionally, the actual dilution factor may be verified by measuring additional dilutions, such as the $8^{th}$ and $9^{th}$ dilutions.

In a third step, the quantified total DNA concentration is used to calculate the sample volume which contains the appropriate amount of total DNA required for gel electrophoresis (e.g., about 500 ng). The corresponding volume is dispensed from the original DNA sample and delivered to the gel for electrophoresis-based DNA quality assessment. In one example, the quality of genomic DNA may be evaluated. In this example, intact genomic DNA appears as a high molecular weight smear on the gel. Degraded genomic DNA appears as fragmented and/or a lower molecular weight smear on the gel.

In a fourth step, another 300-nL DNA sample droplet is dispensed from the sample reservoir and mixed with real-time PCR reagents. The combined droplet and a human and/or a bacterial DNA standard are analyzed by real-time PCR to determine the amount of human DNA in the sample. The gel electrophoresis and real-time PCR reaction may be conducted in parallel provided that the thermal isolation between the agarose gel and the interior of the droplet actuator is sufficient.

7.6 Systems

Referring to FIGS. 1 through 6, as will be appreciated by one of skill in the art, the invention may be embodied as a method, system, or computer program product. Accordingly, various aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

8 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

We claim:

1. An integrated droplet actuator device for conducting molecular assays comprising:
   (a) a top substrate and a bottom substrate, the two substrates configured to form a droplet operations gap;
   (b) electrodes associated with one or both of the bottom substrate and the top substrate, and configured for conducting droplet operations in the gap;
   (c) a gel;
   (d) a pair of electrodes in electrical contact with the gel, the electrodes arranged at first and second locations in relation to the gel;
   (e) one or more fluid paths extending from inside the gap to the gel; and
   (f) at least a first reaction zone and a second reaction zone.

2. The integrated droplet actuator device of claim 1, further comprising one or more loading slots formed in the gel and arranged in fluid connection with one or more of the fluid paths.

3. The integrated droplet actuator device of claim 1, wherein the gel comprises a gel slab.

4. The integrated droplet actuator device of claim 1, wherein the gel slab comprises an electrophoresis gel.

5. The integrated droplet actuator device of claim 1, further comprising at least a first heat source and a second heat source corresponding to the at least first reaction zone and a second reaction zone respectively.

6. The integrated droplet actuator of claim 5, wherein the at least first heat source and second heat source each comprise a heater bar.

7. The integrated droplet actuator of claim 6, wherein each heater bar comprises an aluminum heater bar, the aluminum heater bar further comprising one or more heating resistors and thermistors.

8. The integrated droplet actuator of claim 1, wherein one of the at least first or second reaction zones is heated to a melting temperature.

9. The integrated droplet actuator of claim 8, wherein the melting temperature comprises a temperature sufficient for denaturing of DNA template and primers.

10. The integrated droplet actuator of claim 8, wherein the melting temperature comprises about 95° C.

11. The integrated droplet actuator of claim 1, wherein one of the at least first or second reaction zones is heated to a temperature sufficient for annealing of DNA template and primer extension.

12. The integrated droplet actuator of claim 11, wherein the temperature sufficient for annealing of DNA template and primer extension comprises a temperature in a range of about 55° C. to about 65° C.

13. The integrated droplet actuator of claim 1, wherein the at least first reaction zone and second reaction zone are positioned at a sufficient distance from the gel so as to not affect the gel internal temperature.

14. The integrated droplet actuator device of claim 1, wherein the gel comprises an electrophoresis gel.

15. The integrated droplet actuator device of claim 1, wherein the gel comprises one or more loading slots formed in the gel.

16. The integrated droplet actuator device of claim 15, wherein the one or more loading slots are aligned with and in fluid connection with the one or more fluid paths.

17. The integrated droplet actuator device of claim 15, wherein the one or more loading slots comprise nucleic acid loading slots.

18. The integrated droplet actuator device of claim 15, wherein the one or more loading slots are loaded with a loading buffer.

19. The integrated droplet actuator device of claim 15, wherein the loading buffer is retained in the one or more loading slots by surface tension forces.

20. The integrated droplet actuator device of claim 15, wherein the one or more fluid paths further provide a fluidic path from one or more designated electrodes to one or more corresponding loading spots.

21. The integrated droplet actuator device of claim 15, wherein a microfluidics-gel interface is formed where the one or more fluid paths and the one or more loading slots interface.

22. The integrated droplet actuator device of claim 15, wherein the gel is in electrical contact with a pair of electrodes, wherein the electrodes are arranged at first and second locations in relation to the gel and parallel to the one or more loading slots.

23. The integrated droplet actuator device of claim 1, wherein the pair of electrodes are directly attached to and integrated with the top substrate.

24. The integrated droplet actuator device of claim 1, wherein the pair of electrodes are positioned in a corresponding pair of trenches molded into the gel slab, wherein the trenches are arranged at first and second locations in relation to the gel and facilitate an electrical interface that provides a uniform electrical field in the gel.

25. The integrated droplet actuator device of claim 24, wherein the pair of trenches comprises an electrophoresis buffer.

26. The integrated droplet actuator device of claim 25, wherein electrophoresis buffer comprises Tris-Borate-Edta (TBE).

27. The integrated droplet actuator device of claim 1, wherein the pair of electrodes are arranged at first and second locations in contact with the gel.

28. The integrated droplet actuator device of claim 1, wherein the pair of electrodes comprises platinum wire.

29. The integrated droplet actuator device of claim 1, wherein one of the pair of electrodes is a negative electrode and one of the pair of electrodes is a positive electrode.

30. The integrated droplet actuator device of claim 1, wherein electrophoresis is conducted without submerging the gel in an electrophoresis buffer.

31. The integrated droplet actuator device of claim 1, wherein the gel is arranged in a protruded structure formed on the top substrate.

32. The integrated droplet actuator device of claim 1, wherein the gel is submerged in an electrophoresis buffer during electrophoresis.

33. The integrated droplet actuator device of claim 1, wherein the top substrate and the bottom substrate are attached to one another by an epoxy glue ring.

34. The integrated droplet actuator device of claim 1, wherein the electrodes in part (b) of claim 1 comprise an array of electrodes.

35. The integrated droplet actuator device of claim 1, wherein the electrodes in part (b) of claim 1 comprise a path of electrodes.

36. The integrated droplet actuator device of claim 1, wherein the electrodes in part (b) of claim 1 comprise electrowetting electrodes.

37. The integrated droplet actuator device of claim 1, wherein the bottom substrate comprises a printed circuit board.

38. The integrated droplet actuator device of claim 1, wherein the top substrate comprises a high transparency and low fluorescence plastic material.

39. The integrated droplet actuator device of claim 38, wherein the plastic material is suitable for fluorimeter operation.

40. The integrated droplet actuator device of claim 38, wherein the plastic material comprises cyclo-olefin polymer and/or copolymer.

41. The integrated droplet actuator device of claim 1, wherein the droplet operations gap comprises a filler fluid.

42. The integrated droplet actuator device of claim 41, wherein the filler fluid comprises oil.

43. The integrated droplet actuator device of claim 42, wherein the oil comprises silicone oil.

44. The integrated droplet actuator device of claim 1, wherein the bottom substrate comprises a hydrophobic layer disposed on a surface of the bottom substrate facing the gap.

45. The integrated droplet actuator device of claim 44, wherein the hydrophobic layer is formed on top of the electrodes.

46. The integrated droplet actuator device of claim 1, wherein the top substrate comprises a hydrophobic layer disposed on a surface of the top substrate facing the gap.

47. The integrated droplet actuator device of claim 1, wherein the gel is arranged on the top substrate.

* * * * *